US010729597B2

(12) United States Patent
Cree

(10) Patent No.: US 10,729,597 B2
(45) Date of Patent: Aug. 4, 2020

(54) EMBOSSED TEXTURED WEBS AND METHOD FOR MAKING

(71) Applicant: James W. Cree, Loveland, CO (US)

(72) Inventor: James W. Cree, Loveland, CO (US)

(73) Assignee: ADVANTAGE CREATION ENTERPRISE LLC, Loveland, OH (US)

( * ) Notice: Subject to any disclaimer, the term of this patent is extended or adjusted under 35 U.S.C. 154(b) by 638 days.

(21) Appl. No.: 14/695,263

(22) Filed: Apr. 24, 2015

(65) Prior Publication Data

US 2015/0297420 A1    Oct. 22, 2015

Related U.S. Application Data

(62) Division of application No. 13/259,334, filed as application No. PCT/US2010/000860 on Mar. 24, 2010, now Pat. No. 9,067,334.

(Continued)

(51) Int. Cl.
*A61F 13/512*   (2006.01)
*B29C 59/02*    (2006.01)
(Continued)

(52) U.S. Cl.
CPC ...... *A61F 13/512* (2013.01); *A61F 13/15731* (2013.01); *B26F 1/24* (2013.01);
(Continued)

(58) Field of Classification Search
CPC .. A61F 13/512; A61F 13/15731; B32B 3/266; B32B 3/28; B32B 27/06; B29C 48/0022; B29C 48/08; B29C 48/13; B29C 48/0023; B29C 48/0011; B29C 48/021; B29C 59/022; B29C 59/04; Y10T 156/1056; Y10T 156/1057; Y10T 156/1023; Y10T 428/24273; Y10T 428/24322; B26F 1/18; B26F 1/20; B26F 1/24; B26F 1/26; B31F 1/07; B31F 2201/0738; B31F 2201/0743;
(Continued)

(56) References Cited

U.S. PATENT DOCUMENTS 3,719,736 A    3/1973 Woodruff
3,881,489 A    5/1975 Hartwell
(Continued)

FOREIGN PATENT DOCUMENTS

CN    1059765 A    3/1992
CN    1705464      12/2005
(Continued)

OTHER PUBLICATIONS

JWC-005-PCT—ISR WO—PCT/US2010/000860 PCT International Search Report and Written Opinion dated Jun. 22, 2010 on corresponding PCT application (6 pages).
(Continued)

*Primary Examiner* — Maria V Ewald
*Assistant Examiner* — Ethan Weydemeyer
(74) *Attorney, Agent, or Firm* — Donald E. Hasse; Hasse & Nesbitt LLC

(57) ABSTRACT

Methods, apparatus and articles of manufacture are shown for creating a soft textile expanded apertured film.

19 Claims, 2 Drawing Sheets

Related U.S. Application Data

(60) Provisional application No. 61/162,969, filed on Mar. 24, 2009.

(51) Int. Cl.

| | | |
|---|---|---|
| *A61F 13/15* | (2006.01) | |
| *B29C 59/04* | (2006.01) | |
| *B32B 3/26* | (2006.01) | |
| *B32B 27/06* | (2006.01) | |
| *B26F 1/24* | (2006.01) | |
| *B32B 3/28* | (2006.01) | |
| *B29C 48/08* | (2019.01) | |
| *B29C 48/00* | (2019.01) | |
| *B29C 48/13* | (2019.01) | |
| *B26D 7/00* | (2006.01) | |
| *A61F 13/51* | (2006.01) | |
| *B29K 23/00* | (2006.01) | |

(52) U.S. Cl.
CPC ............ *B29C 59/022* (2013.01); *B29C 59/04* (2013.01); *B32B 3/266* (2013.01); *B32B 3/28* (2013.01); *B32B 27/06* (2013.01); *A61F 13/51* (2013.01); *A61F 2013/51078* (2013.01); *B26D 2007/0093* (2013.01); *B29C 48/0011* (2019.02); *B29C 48/0021* (2019.02); *B29C 48/0022* (2019.02); *B29C 48/0023* (2019.02); *B29C 48/08* (2019.02); *B29C 48/13* (2019.02); *B29C 2793/0045* (2013.01); *B29K 2023/00* (2013.01); *B32B 2250/02* (2013.01); *B32B 2307/726* (2013.01); *B32B 2555/02* (2013.01); *Y10T 428/24273* (2015.01); *Y10T 428/24322* (2015.01)

(58) Field of Classification Search
CPC ...... B31F 2201/0797; B31F 2201/0748; B31F 2201/0741
See application file for complete search history.

(56) References Cited

U.S. PATENT DOCUMENTS

| | | |
|---|---|---|
| 3,957,414 A | 5/1976 | Bussey, Jr. et al. |
| 4,128,679 A | 12/1978 | Pohland |
| 4,223,063 A | 9/1980 | Sabee |
| 4,276,336 A | 6/1981 | Sabee |
| 4,285,100 A | 8/1981 | Schwarz |
| 4,333,979 A | 6/1982 | Sciaraffa et al. |
| 4,609,518 A | 9/1986 | Curro et al. |
| 4,629,643 A | 12/1986 | Curro et al. |
| 4,780,352 A | 10/1988 | Palumbo |
| 4,886,632 A | 12/1989 | Van Iten et al. |
| 4,950,264 A | 8/1990 | Osborn, III |
| 4,995,930 A | 2/1991 | Merz et al. |
| 5,009,653 A | 4/1991 | Osborn, III |
| 5,158,819 A | 10/1992 | Goodman |
| 5,336,545 A | 8/1994 | Morman |
| 5,368,909 A | 11/1994 | Langdon et al. |
| 5,383,869 A | 1/1995 | Osborn, III |
| 5,399,174 A | 3/1995 | Yeo et al. |
| 5,418,045 A | 5/1995 | Pike et al. |
| 5,422,172 A | 6/1995 | Wu |
| 5,494,736 A | 2/1996 | Willey et al. |
| RE35,206 E | 4/1996 | Hassenboehler, Jr. et al. |
| 5,567,376 A | 10/1996 | Turi et al. |
| 5,575,786 A | 11/1996 | Osborn, III |
| 5,591,149 A | 1/1997 | Cree et al. |
| 5,626,571 A | 5/1997 | Young et al. |
| 5,656,119 A | 8/1997 | Srinivasan et al. |
| 5,674,211 A | 10/1997 | Ekdahl |
| 5,674,216 A | 10/1997 | Buell et al. |
| 5,693,037 A | 12/1997 | Lee et al. |
| 5,695,377 A | 12/1997 | Triebes et al. |
| 5,814,389 A | 9/1998 | Giacometti |
| 5,851,935 A | 12/1998 | Srinivasan et al. |
| 5,882,769 A | 3/1999 | McCormack et al. |
| 5,997,986 A | 12/1999 | Turi et al. |
| 6,015,764 A | 1/2000 | McCormack et al. |
| 6,069,097 A | 5/2000 | Suzuki et al. |
| 6,106,925 A | 8/2000 | Palumbo |
| 6,190,602 B1 | 2/2001 | Blaney et al. |
| 6,228,462 B1 | 5/2001 | Lee et al. |
| 6,286,145 B1 | 9/2001 | Welchel et al. |
| 6,300,257 B1 | 10/2001 | Kirchberger et al. |
| 6,353,149 B1 | 3/2002 | Stone |
| 6,376,095 B1 | 4/2002 | Cheung et al. |
| 6,395,211 B1 | 5/2002 | Dettmer et al. |
| 6,452,064 B1 | 9/2002 | Thoren et al. |
| 6,537,644 B1 | 3/2003 | Kauschke et al. |
| 6,610,904 B1 | 8/2003 | Thomas et al. |
| 6,700,036 B2 | 3/2004 | Thomas et al. |
| 6,703,115 B2 | 3/2004 | Hale et al. |
| 6,720,279 B2 | 4/2004 | Cree et al. |
| 6,739,024 B1 | 5/2004 | Wagner |
| 6,752,947 B1 | 6/2004 | Lanigan et al. |
| 6,849,319 B2 | 2/2005 | Cree et al. |
| 6,942,748 B2 | 9/2005 | Cree et al. |
| 6,942,896 B2 | 9/2005 | Martin |
| 7,037,569 B2 | 5/2006 | Curro et al. |
| 7,204,907 B2 | 4/2007 | Cree et al. |
| 7,476,632 B2 | 1/2009 | Olson et al. |
| 7,625,829 B1 | 12/2009 | Cree et al. |
| 7,695,799 B2 | 4/2010 | Cree |
| 7,713,683 B2 | 5/2010 | Gray et al. |
| 8,182,728 B2 | 5/2012 | Cree et al. |
| 8,241,543 B2 | 8/2012 | O'Donnell et al. |
| 2002/0098341 A1 | 7/2002 | Schiffer et al. |
| 2002/0160085 A1 | 10/2002 | Tokita et al. |
| 2003/0017345 A1 | 1/2003 | Middlesworth et al. |
| 2003/0125688 A1 | 7/2003 | Keane et al. |
| 2003/0225383 A1 | 12/2003 | Glaug et al. |
| 2004/0005457 A1 | 1/2004 | Delucia et al. |
| 2004/0121687 A1 | 6/2004 | Morman et al. |
| 2004/0161586 A1* | 8/2004 | Cree .................. A61F 13/537 428/131 |
| 2005/0064136 A1* | 3/2005 | Turner ............... A61F 13/15731 428/131 |
| 2005/0106980 A1 | 5/2005 | Abed et al. |
| 2005/0124251 A1 | 6/2005 | Tsai et al. |
| 2005/0214506 A1 | 9/2005 | Lee et al. |
| 2005/0241750 A1 | 11/2005 | McCormack et al. |
| 2006/0087053 A1 | 4/2006 | O'Donnell et al. |
| 2006/0234586 A1 | 10/2006 | Wong et al. |
| 2007/0029694 A1 | 2/2007 | Cree et al. |
| 2007/0048498 A1 | 3/2007 | Cree |
| 2007/0123124 A1 | 5/2007 | Middlesworth et al. |
| 2007/0237924 A1 | 10/2007 | Bruce et al. |
| 2007/0249253 A1 | 10/2007 | Angeli et al. |
| 2007/0250026 A1 | 10/2007 | Venturino et al. |
| 2007/0259154 A1 | 11/2007 | Cree |

FOREIGN PATENT DOCUMENTS

| | | |
|---|---|---|
| DE | 197 50 459 | 5/1999 |
| DE | 100 08 827 | 9/2001 |
| EP | 0164740 | 12/1985 |
| EP | 0360929 | 4/1990 |
| EP | 0749739 B1 | 11/2000 |
| EP | 1712667 A1 | 10/2006 |
| GB | 2 282 990 | 4/1995 |
| WO | WO 92/00050 | 1/1992 |
| WO | WO 98/55295 | 12/1998 |
| WO | WO 99/65673 | 12/1999 |
| WO | WO 00/04215 | 1/2000 |
| WO | WO 2004/007158 | 1/2004 |
| WO | WO 2004/058121 | 7/2004 |
| WO | WO 2008051548 | 5/2008 |

OTHER PUBLICATIONS

JWC-005 PCT—IPRP—PCT/US2010/000860 PCT International Preliminary Report on Patentability dated Oct. 6, 2011 on corresponding PCT application (6 pages).

(56) References Cited

OTHER PUBLICATIONS

JWC-005 EP—EP 10756471.8—EP Communication dated Jun. 17, 2014 (1 page) with attached Supplemental European Search Report dated Jun. 6, 2014 (6 pages). (7 total pages).
JWC-005 CN—CN 201080022321.1 First Office Action dated Dec. 27, 2013 (8 pages) with English translation (11 pages). (19 pages total).
JWC-005 CN—CN 201080022321.1 Second Office Action dated Nov. 13, 2014 (6 pages) with English translation (9 pages). (15 pages total).
JWC-005 CN—CN 201080022321.1 Notification of Grant Patent Right dated Jul. 22, 2015 (2 pages) with English translation (2 pages). (4 total pages).
JWC-003 PCT—ISRWO—PCT/US2010/061084 PCT International Search Report and Written Opinion dated Sep. 8, 2011 on corresponding PCT application (11 pages).
JWC-003 PCT—IPRP—PCT/US2010/061084 PCT International Preliminary Report on Patentability dated Jun. 28, 2012 on corresponding PCT application (7 pages).
JWC-003 EP—ESR—EP 10 838 305 EP Communication dated Jan. 27, 2014 (1 page) with attached Supplemental European Search Report dated Jan. 16, 2014 (3 pages). (4 total pages).
JWC-003 CN—CN 201080064255.4 First Office Action dated Jan. 6, 2014 (English translation 3 pages total).
JWC-003 CN—CN 201080064255.4 Second Office Action dated Sep. 23, 2014 (English translation 8 pages total).
JWC-003 CN—CN 201080064255.4 Third Office Action dated Apr. 15, 2015 (English translation 12 pages total).
First Office Action from the State Intellectual Property Office for corresponding JWC-005D Chinese Application No. 201510617125.3 (5 pages) with English translation (7 pages), and English translation of pending Claims 1-10.

* cited by examiner

EMBOSSED TEXTURED WEBS AND METHOD FOR MAKING

CROSS REFERENCE TO RELATED APPLICATIONS

This application is a divisional application of U.S. application Ser. No. 13/259,334 (pending), filed Sep. 23, 2011 which is a continuation of International Application No. PCT/US2010/000860, filed Mar. 24, 2010, which claims the benefit of Provisional Application No. 61/162,969, filed Mar. 24, 2009, the disclosures of which are incorporated herein by reference in their entirety.

FIELD OF THE INVENTION

The present invention relates to textured apertured films with an embossing pattern and methods for making such webs.

BACKGROUND OF THE INVENTION

Apertured films are used in various industrial and consumer products sectors. For example, apertured films are used to produce disposable sheets, disposable garments and hygiene and sanitary products, such as sanitary napkins, incontinence pads and baby diapers.

Apertured films can be manufactured using various techniques. For example, one technique for forming apertured webs entails extruding a plastic sheet of film using traditional film extrusion techniques (for example, a thin sheet of LDPE delivered through a cast or blown extrusion head) and aperturing the film using solid or molten phase forming techniques as known in the art (e.g., heat and differential pressure via vacuum as described in U.S. Pat. No. 3,957,414 to Bussey et. al.; water perforation techniques as described in U.S. Pat. No. 4,609,518 to Curro et. al.; thermo-mechanical contact perforation (e.g., pin perforation, engraved cylinders, etc. often in contact with smooth cylinders as described in U.S. Pat. No. 5,814,389 to Giacometti, U.S. Pat. No. 4,128,679 to Pohland, U.S. Pat. No. 4,886,632 to Van Iten, etc.) In some instances, the film may be textured prior to perforation via mechanical or water embossing, or other methods as are known in the art.

However limitations of current topsheets include providing softness appropriate to skin contact while still absorbing fluid and maintaining the feeling and conveying the sensation of dryness. Often, as a consequence, dryness is maintained but the topsheet web and/or a product made from the web isn't perceived as soft—the web or product may have a stiff, scratchy or similar, generally unpleasant, sensation. Conversely a web or product may obtain desired softness but provide an uncomfortable wetness sensation.

DETAILED DESCRIPTION OF THE PREFERRED EMBODIMENTS

As used herein, the term "machine direction" means the direction in which webs are formed, which is the longitudinal direction of an uncut web.

As used herein, the term "transverse direction" means the cross direction, disposed at 90.degree. to the machine direction, and extending across the width of the initially formed precursor web.

A topsheet is provided in various embodiments. As used herein the term "topsheet" or, following aperturing as further described below, "Apertured Topsheet," refers to a polymeric film web and preferably a thermoplastic polyolefenic high wettable film sheet or web extruded using traditional film extrusion techniques well known in the art. Typical polyolefin blends are derived from resins such as LDPE, LLDPE, HDPE and metallocene based m-LDPE, and blends can also include a variety of other resins such as polyproplene; ethylene-polypropylene copolymers, ethylene vinyl acetate, calcium carbonate, barium sulfate.

It may be desired in certain embodiments to make such film hydrophilic. This may be done by either inserting a surfactant in the resin prior to extrusion or by spraying the web at some point after extrusion, e.g., possibly after perforation with a surfactant. Typical resin incorporated surfactants used include siliconized low molecular weight polymers or fatty acids with ester such as sorbitan ester surfactants.

Figure 1:
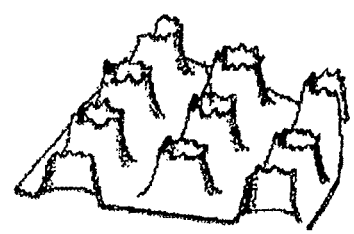
FIG. 1 shows a partial cutaway view of a partial embodiment.

After extrusion of the topsheet, the film is apertured using solid or molten phase forming techniques as known in the art, e.g., through heat and/or pressure differential, water perforation, etc. which provides conical perforations in the web extending outward, away from a first plane of the web. As seen in FIG. 1, the perforations are usually in conical shape with an open end at their top, and exhibit textile-like or cloth-like feel when touched. The cones' density on the web varies from 35 perforations per linear inch to 80 perforations per linear inch which provides a textile like surface. Also shown is a second plane of the web.

Embodiments used in absorbent articles may have a topsheet separating the remainder of the absorbent article from the skin as the cones on the topsheet ascend or point toward the wearer side.

As is further described below, an absorbent core is provided in various embodiments as well. As used herein the term absorbent core may comprise one or more layers engineered to absorb and store body exudates and other desired fluids. As known in the art absorbent layers can be made of a variety of fibrous or porous foraminous absorbent foam materials or fibrous absorbents including short natural cellulosic fiber layers, synthetic fibrous webs made of fibers that are PP, PE, PET, Acetate or a combination of such polymers. Synthetic fibers are typically sold as a consolidated web—comprised of more than one layer—using various consolidation techniques known in the art, e.g., thermobonding airlaid, thermobonded spunlaid, airthrough bonding airlaid, etc. Embodiments may provide an absorbent layer with an attachment affinity to the apertured film used.

Various embodiments typically provide the absorbent core in roll form. Embodiment may use part of an absorbent core as well. So for example, an embodiment is comprised of an absorbent core layer that is made with a thermobonded fibrous carded PP/PE nonwoven with a basis weight ranging between 10 and 60 gsm. Sanitary napkin and other embodiments may use a more or less full absorbent core, which is typically made of a combination of the above described absorbent layer and a thermobonded airlaid core with a basis weight of between 30 and 200 gsm.

Embodiments may provide for the aperturing and subsequent processing as further described below to take place on manufacturing lines of various types. Those types include wide web lamination lines, article manufacturing lines, including converting and absorbent article manufacturing lines. So for example, embodiments may be provided in a diaper or napkin manufacturing line, retrofitted in an existing converting line, etc.

Figure 2:
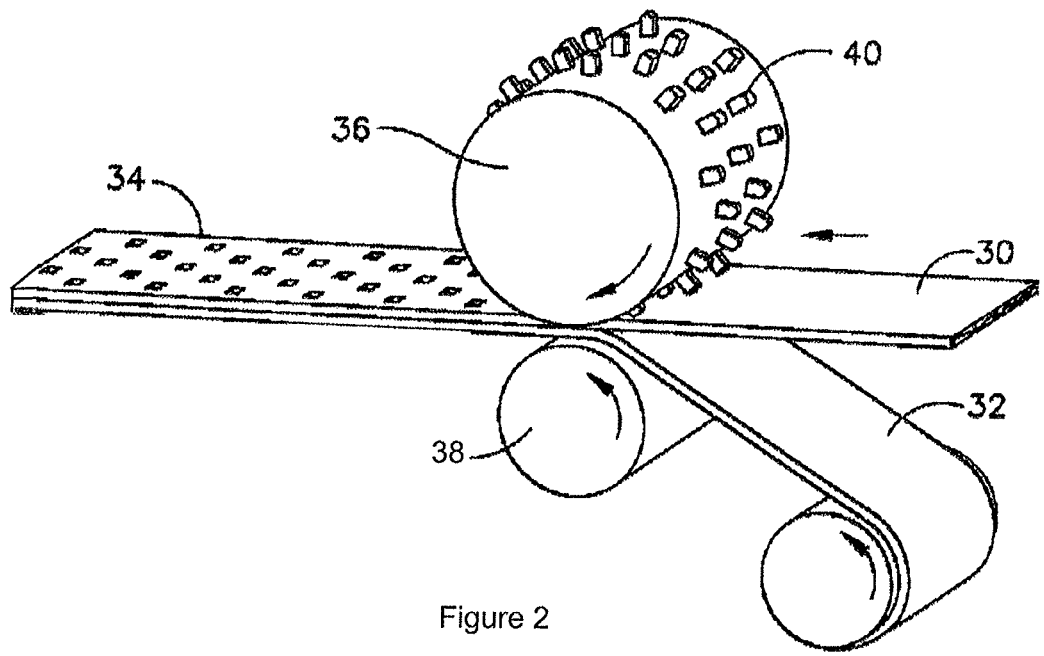
FIG. 2 shows a roller station embodiment.

Whether embodiments are inserted into article manufacturing lines or not, following aperturing, embodiments provide for embossing of the apertured web, as is shown for example, in the embodiment of FIG. 2. FIG. 2 shows the apertured web 30, with a second web 32, which is an absorbent core layer. The webs travel between patterned embossing roll 36 and smooth support roll 38 where the embossing occurs on apertured web 30, towards the plane from which the perforations are extending, and so providing a footprint impression of at least $\frac{1}{1000}$ of an inch in the web, which comprises a raised area, extending away from the other plane of the web against web 32. In embodiments with a support web, the footprint will extend into the support web.

Figure 3:
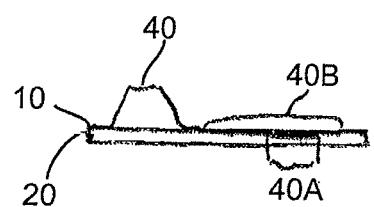
FIG. 3 is a cutaway article embodiment.

As the embossing occurs, at least some of the apertures or cones (not seen) on web 30, which depend away from the top plane of the film web, encounter the raised pattern of embossing (e.g., 40) projecting outwardly from the embossing roll 36. This contact results in expanding of the web, flattening of those apertures, the land areas about the apertures, thinning of the web and the absorbent core layer, and expansion of the film web, providing a footprint impression (e.g., 40B in FIG. 3) at a depth of at least $\frac{1}{1000}^{th}$ of an inch, into the web 32. Turning briefly to FIG. 3, a cutaway view of the effect of the footprint both on a perforation (see, e.g., 40A) and generally on the web 10 is shown.

Figure 4:
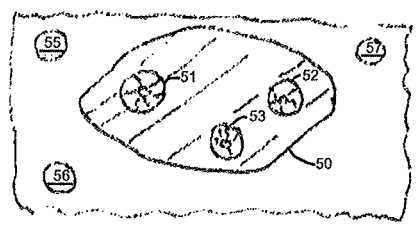
FIG. 4 is a top view article embodiment.

FIG. 4 shows a top view of the footprint of a projection of the raised engraved embossed pattern of the embossing roll. Area 50 is the footprint, and also shown are flattened perforations 51, 52 and 53 and land areas (not labeled) between the perforations. Remaining are perforations 55, 56 and 57 which were not flattened as they fell outside the footprint of a projection of a embossing roller.

It should be noted that, although embossing rollers have been described in various embodiments herein, other methods of embossing known in the art may be used in various embodiments, for example ultrasound embossing, including ultrasound horn embossing, etc. and may be provided so as to be placed in an article line, converting line, wide web line, etc. as known in the art. These and other embodiments may provide pressure as well as heat to emboss.

Figure 5:
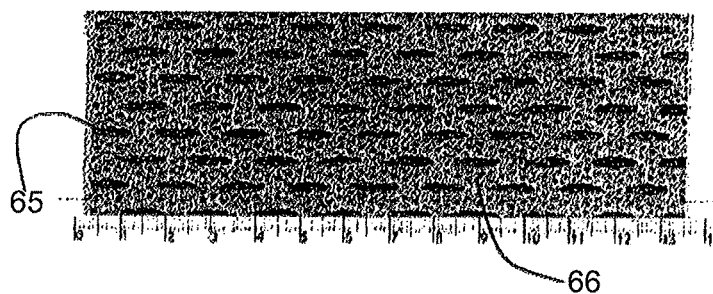
FIG. 5 is a photograph of an article embodiment.

FIG. 5 shows a photograph of an embodiment taken as a top view. Both footprints, see e.g., 65, and perforations, see e.g., 66, are visible. What are not visible are the flattened perforations such as 51, 52 and 53 in FIG. 4 due to contrast on the photograph.

An apertured web with embossing provides a textured expanded apertured web textile like product, with a thinner film web about the footprint area. As a result a visually attractive article is provided. The underlying absorbent core is visible providing the wearer with reassurance. Moreover, softness, flexibility and ductility is also provided in the combined web. The entire article appears softer as the inter-layer attachment—between the apertured topsheet and absorbent core—only takes place at embossing sites, which provides comfort to the wearer and perforations that remain between the footprints provide tactile softness as they project towards the wearer's skin. The inter-layer attachments at the embossing sites also provide flexibility and ductility as their limited sites of attachment provide the combined web with degrees of flexibility and ductility that might otherwise be lacking.

Embossing serves to help attach the apertured web to the absorbent core. Flattening of the perforations provides cones that are flattened. Thus the flattened open hole of a perforation through embossing provides at least some attachment of the film to the core layer as the area about the top hole of a flattened perforation becomes entangled with the absorbent core web after downward pressure—that is, pressure against the projecting perforation imposed by the projections on the embossing roller. The pressure, as measured against a flat support roller or other substrate, is usually in the range of 100 to 175 psi, however, it may be up to 400 psi. Moreover, the pressure also imposes at least some melting of the web film, including the perforations and the surrounding land areas as well as the corresponding area of the absorbent core layer in the area under the footprint providing for attachment.

The rollers in this and other embodiments may be heated and/or apply heat, which will provide for further melting and may assist entanglement as well. For example, in an embodiment the embossing roller is typically heated to a temperature similar to the softening point of the topsheet, which is usually greater than 80 degrees C. but less than 200 degrees C. Thus in this, similar thermo mechanical pressure and other embodiments attachment is provided as a result of a combination of pressure and heat, providing attachment though melting and entanglement as was described above, as well as footprints with associated visible attractiveness, performance signaling, softness, flexibility and ductility.

Fluids deposited on the topsheet will be drawn into the absorbent core primarily through the raised perforated apertures. These also, because of their raised appearance, provide peaks and valley, helping prevent the fluid from running away, by capturing the fluid and channeling it to the absorbent core. Those flattened apertures—those which have been subject to embossing—may provide some channeling for fluids, as well, through capillary and other action, and also provide fastening to the absorbent core as is further described herein.

Embodiments also include embossing on an absorbent article manufacturing or converting line or lines, including high speed manufacturing lines. The rollers may be set as desired on the line, with appropriate placement of the embossing roller. It should be noted that embodiments with embossing may be provided to the topsheet alone, to a semi finished product consisting of the film and an absorbent core comprised of one or more layers, or to a finished product prior to a final cutting. If embossing occurs to the topsheet itself, the film will then have a footprint area, without of course attendant attachment to an underlying web through the flattened apertures.

Figure 6:
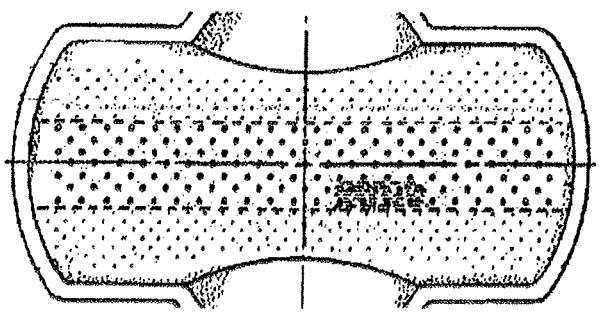
FIG. 6 is a top partial view of an article embodiment.

It may be desired in certain preferred embodiments to define various areas of a web through embossing. For example, patterns or other areas may be interposed through perforations and embossing; different embossing cylinders may provide for varying sizes, shapes, or other parameters in whole or part. For example, an embodiment such as that shown in FIG. 6 may provide greater macroscopic embossing in the middle of an absorbent pad—providing higher absorbency by allowing the fluid to pool in the embossing regions of the topsheet before being absorbed by the flattened apertures. The edge, without embossing, but will provide absorption through its raised apertures.

Embodiments may also be subsequently finished, semi finished, or treated in some manner, e.g., a film with fiber like surface, expanding a textile like apertured film, etc. Further treatment may also be desired. For example lotion can be applied, semi-curable nano fiber included in the embossing zones, the shape of the apertures could be altered using processes such as mechanical activation, the distance between the embossing zones and the apertures modified, again through activation or other means as known in the art, etc. Combinations of various post embossing treatment techniques can be used as well in various embodiments.

Embodiments may also be combined with a component or components to form laminate or composite materials, finished and semi-finished, etc. which, if desired, may be further treated through embossing, perforating etc. sewing, bonding, printing, cutting, shaping, gluing, fluting, sterilizing, etc. combination with or independently of other processes as are known in the art.

In one embodiment an apertured topsheet is provided from XIAMEN YANJAN INDUSTRY CO Ltd., a perforated film company located in Xiamen province China under the tradename SC100 (www.yanjan.com.) The apertured topsheet is provided in roll form. The roll is unwound on a napkin converting line, coming into contact with a through air carded absorbent nonwoven. The nonwoven is comprised of a blend of BicoPP and PE and has a basis weight of 40 gsm and is supplied by Chisso Corporation Moriyama Japan. The nonwoven if generally sourced under the designation "Acquisition Distribution Layer" or ADL as known in the art.

The topsheet and nonwoven are embossed at a temperature of 95 degrees C. by a roll (provided by Ungricht-Richtung Industries) with heated raised ellipse shaped projections. The projections are provided in the machine direction with the distance between each set of protuberances being not less than 2 mm.

This embodiment is patterned as well, and the embossing area within the confines of the center of the sanitary napkin pad is 80 mm or less. After embossing, the combined web is provided with further layers of an absorbent core, as well as a backsheet, attached by crimping, and the embossed article is cut and completed.

It may be desired in various embodiments to use various patterns, in whole or part, in various types of articles, including adult, child or infant incontinence products (for example, diapers, briefs, etc.) female hygiene products (for example, female menstrual products, sanitary napkins, pantiliners, etc.) wraps, including sterile and nonsterile (e.g. bandages with and without absorbent sections) as well as other disposable and/or multiple use products; e.g., articles proximate to a human or animal body, such as for example, garments, apparel, including undergarments, under- and outer-wear, for example, undershirts, bras, briefs, panties, etc., bathing suits, coveralls, socks, head coverings and bands, hats, mitten and glove liners, medical clothing, etc.; bed sheets; medical drapes; packaging materials; protective covers; household; office; medical or therapeutic devices and wraps.

Although the present invention has been described with respect to various specific embodiments, various modifications will be apparent from the present disclosure and are intended to be within the scope of the following claims.

What is claimed is:

1. A textured film topsheet made by a method comprising:
aperturing a polymeric film web having first and second planes by a solid or molten phase forming technique, the aperturing forming open conical perforations which extend outward beginning from the first web plane and which are spaced at a density of between 35-80 perforations per linear inch; and
embossing the apertured web by contact with a patterned embossing roll that is heated and/or applies heat, facing the first web plane so as to flatten some of the perforations and provide inter-layer attachment to an underlying absorbent core at embossing sites, spaced projections of the embossing roll leaving footprint impressions of at least $1/1000$ of an inch in said web extending away from the second web plane, wherein each footprint impression provides a flattened first web plane land area comprising flattened conical perforations so as to leave unflattened conical perforations outside of each footprint, and wherein body fluid deposited on the textured film topsheet passes through the textured film topsheet to the absorbent core primarily through the open conical perforations.

2. The textured film topsheet as in claim 1, wherein the film web is a thermoplastic film and the film web is joined with a support web during said embossing.

3. The textured film topsheet as in claim 1, wherein said embossing occurs with the film web against an absorbent core layer and the footprint impression extends into the absorbent core layer.

4. The textured film topsheet as in claim 3, wherein said embossing flattens land area between the flattened perforations and thins at least some of the film web and absorbent core layer while also expanding at least some of the film web.

5. An article comprising the textured film topsheet as in claim 1 and an absorbent core.

6. A diaper or napkin comprising the textured film topsheet as in claim 1 and an absorbent core attached thereto.

7. The textured film topsheet as in claim 1, wherein the solid or molten phase forming technique comprises a heat and pressure differential technique or a water perforation technique.

8. The textured film topsheet as in claim 1, wherein the textured film is an absorbent topsheet.

9. The textured film topsheet as in claim 1, wherein said embossing occurs in a nip formed between the embossing roll and a smooth support roll.

10. The textured film topsheet as in claim 1, wherein the embossing roll is heated to a temperature greater than 80 degrees C. but less than 200 degrees C.

11. The textured film topsheet as in claim 1, wherein a distance between the projections is not less than 2 mm.

12. The textured film topsheet as in claim 3, wherein said embossing provides entanglement of open holes of flattened perforations with the absorbent core layer.

13. The textured film topsheet as in claim 1, wherein said embossing applies a pressure of 100-175 psi.

14. The textured film topsheet as in claim 3, wherein said embossing imposes at least some melting of the film web including at the flattened land areas, the flattened perforations, and a corresponding area of the absorbent core layer underneath the footprint.

15. An article comprising an absorbent core and a textured film topsheet made by a method comprising:
aperturing a polymeric film web having first and second planes by a solid or molten phase forming technique, the aperturing forming open conical perforations which extend outward beginning from the first web plane and which are spaced at a density of between 35-80 perforations per linear inch; and
embossing the apertured web by contact with a patterned embossing roll facing the first web plane so as to flatten some of the perforations, spaced projections of the embossing roll leaving footprint impressions of at least $1/1000$ of an inch in said web extending away from the second web plane, wherein each footprint impression provides a flattened first web plane land area comprising flattened conical perforations so as to leave unflattened conical perforations outside of each footprint.

16. The article as in claim 15, wherein the film web is a thermoplastic film and the film web is joined with a support web during said embossing.

17. The article as in claim 15, wherein said embossing occurs with the film web against an absorbent core layer and the footprint impression extends into the absorbent core layer.

18. The article as in claim 17, wherein said embossing flattens land area between the flattened perforations and thins at least some of the film web and absorbent core layer while also expanding at least some of the film web.

19. A diaper or napkin comprising an absorbent core and a textured film topsheet made by a method comprising:

apertureing a polymeric film web having first and second planes by a solid or molten phase forming technique, the aperturing forming open conical perforations which extend outward beginning from the first web plane and which are spaced at a density of between 35-80 perforations per linear inch; and embossing the apertured web by contact with a patterned embossing roll facing the first web plane so as to flatten some of the perforations, spaced projections of the embossing roll leaving footprint impressions of at least $1/1000$ of an inch in said web extending away from the second web plane, wherein each footprint impression provides a flattened first web plane land area comprising flattened conical perforations so as to leave unflattened conical perforations outside of each footprint, wherein said embossing occurs with the film web against an absorbent core layer and the footprint impression extends into the absorbent core layer.

\* \* \* \* \*